US012604871B2

(12) United States Patent
Rousset et al.

(10) Patent No.:  US 12,604,871 B2
(45) Date of Patent:  Apr. 21, 2026

(54) ANIMAL MODEL FOR AMPLIFYING HUMAN OR ANIMAL CIRCULATING TUMOR CELLS

(71) Applicants: INOVOTION, La Tronche (FR); HOSPICES CIVILS DE LYON, Lyons (FR); UNIVERSITE CLAUDE BERNARD LYON 1, Villeurbanne (FR)

(72) Inventors: Xavier Rousset, Saint Martin d'Heres (FR); Emilien Dosda, Chirens (FR); Jean Viallet, Saint Martin d'Heres (FR); Léa Payen-Gay, Caluire et Cuire (FR); Denis Maillet, Lyons (FR)

(73) Assignees: Inovotion, La Tronche (FR); Hospices Civils De Lyon, Lyons (FR); Universite Claude Bernard Lyon 1, Villeurbanne (FR)

( * ) Notice: Subject to any disclaimer, the term of this patent is extended or adjusted under 35 U.S.C. 154(b) by 1092 days.

(21) Appl. No.: 17/289,188

(22) PCT Filed: Oct. 29, 2019

(86) PCT No.: PCT/FR2019/052571
§ 371 (c)(1),
(2) Date: Apr. 27, 2021

(87) PCT Pub. No.: WO2020/089560
PCT Pub. Date: May 7, 2020

(65) Prior Publication Data
US 2022/0007620 A1     Jan. 13, 2022

(30) Foreign Application Priority Data
Oct. 29, 2018    (FR) ...................................... 1859992

(51) Int. Cl.
*A01K 67/0271*      (2024.01)
*C12N 5/09*        (2010.01)

(52) U.S. Cl.
CPC ........ *A01K 67/0271* (2013.01); *C12N 5/0693* (2013.01); *A01K 2207/12* (2013.01); *A01K 2227/30* (2013.01); *A01K 2267/0331* (2013.01); *A01K 2267/0393* (2013.01)

(58) Field of Classification Search
None
See application file for complete search history.

(56) References Cited

U.S. PATENT DOCUMENTS 6,228,345 B1     5/2001  Ossowski

FOREIGN PATENT DOCUMENTS

| WO | WO-2006001021 A2 | 1/2006 |
| WO | WO 2017/079646 | 5/2017 |
| WO | WO 2017/103025 | 6/2017 |

OTHER PUBLICATIONS

Cordero et al J Exp Zool B Mol Dev Evol. 338:447-459 (Year: 2022).*

Ribatti Exp. Cell Res. , 328,314-324 (Year: 2014).*

Doege et al Methods Protoc. , 5, 21., 1-11 (Year: 2022).*

Kundekova Biology , 10, 301. 1-24 (Year: 2021).*

Crespo Bio-protocol, 6 (20): e1962, 1-11 (Year: 2016).*

Debord et al Am J Cancer Res ;8(8):1642-1660 (Year: 2018).*

Williams et al Journal of Visualized Experiment, e53182, 1-6 (Year: 2015).*

Menen et al Anticancer Res. 31, 3125-3128 (Year: 2011).*

Hodgkinson et al Nature Medicine, 20(8), 897-903 (Year: 2014).*

Giannopoulou et al Int. J. Cancer: 94, 690-698 (Year: 2001).*

Kaufman et al Am J Pathol ; 32: 271-285 (Year: 1956).*

Menen et al., *Inhibition of Metastasis of Circulating Human Prostate Cancer Cells in the Chick Embryo by an Extracellular Matrix Produced by Foreskin Fibroblasts in Culture*, 32 Anticancer Research 1573-1578 (2012).

Crespo et al., *The Chick Embryo Choriallantoic Membrane as an in vivo Model to Study Metastasis*, 6(20) Bio-Protocol 1-11 (2016).

Deryugina et al., *Chick embryo chorioallantoic membrane model systems to study and visualize human tumor cell metastasis*, 130 Histochem Cell Biol. 1119-1130 (2008).

Drapkin et al., *Genomic and Functional Fidelity of Small Cell Lung Cancer Patient-Derived Xenografts*, 8(5) Cancer Discovery 600-615 (2018).

Giuliano et al., *Circulating and disseminated tumor cells from breast cancer patient-derived xenograft-bearing mice as a novel model to study metastasis*, 17(3) Breast Cancer Research 1-9 (2015).

Gou et al., *Differences in Driver Genes Between Smoking-Related and Non-Smoking-Related Lung Cancer in the Chinese Population*, Cancer 3069-3079 (Sep. 1, 2015).

Hodgkinson et al., *Tumorigenicity and genetic profiling of circulating tumor cells in small-cell lung cancer*, Nature Medicine 1-9 (Jun. 1, 2014).

Hou et al., *Isolation and retrieval of circulating tumor cells using centrifugal forces*, 3(1259) Scientific Reports 1-8 (Feb. 12, 2013).

International Search Report issued in PCT/FR2019/052571 (Jul. 24, 2020).

Jayachandran et al., *Embryonic chicken transplantation is a promising model for studying the invasive behavior of melanoma cells*, 5(36) Frontiers in Oncology 1-7 (Feb. 2015).

Kagan et al., *A Sample Preparation and Analysis System for Identification of Circulating Tumor Cells*, 25(1) Journal of Clinical Ligand Assay 104-110 (Spring 2002).

(Continued)

*Primary Examiner* — Anoop K Singh
(74) *Attorney, Agent, or Firm* — Panitch Schwarze Belisario & Nadel LLP; Erin M. Dunston

(57) ABSTRACT

The present invention relates to an avian model enabling the amplification of human or animal circulating tumour cells (CTC) and to the use thereof for monitoring and determining the sensitivity of a patient or an animal suffering from cancer to one or more therapeutic agent(s), as well as for screening novel therapeutic agents intended for the treatment of cancer.

6 Claims, 7 Drawing Sheets

(56)　　　　　References Cited

OTHER PUBLICATIONS

Khoo et al., *Expansion of patient-derived circulating tumor cells from liquid biopsies using a CTC microfluidic culture device,* 13(1) Nature Protocols 34-58 (2018).

Kowalik et al., *Current approaches for avoiding the limitations of circulating tumor cells detection methods-implications for diagnosis and treatment of patients with solid tumors,* 185 Translation Research 58-84 (2017).

Laget et al., *Technical Insights into Highly Sensitive Isolation and Molecular Characterization of Fixed and Live Circulating Turmor Cells for Early Detection of Tumor Invasion,* 12(1): e0169427 PLOS One 1-49 (Jan. 6, 2017).

Mangir et al., *An Improved In Vivo Methodology to Visualise Tumour Induced Changes in Vasculature Using the Chick Chorionic Allantoic Membrane Assay,* 32 In Vivo 461-472 (2018).

Mogi et al., *TP53 Mutations in Nonsmall Cell Lung Cancer,* 2011 (Article ID 583929) Journal of Biomedicine and Biotechnology 1-9 (2011).

Nagrath et al., *Isolation of rare circulating tumour cells in cancer patients by microchip technology,* 450(7173) Nature 1235-1239 (Dec. 20, 2007).

Pantel et al., Functional Studies on Viable Circulating Tumor Cells, 62(2) Clinical Chemistry 328-334 (2016).

Ribatti, D., *The chick embryo chorioallantoic membrane as a model for tumor biology,* 328 Experimental Cell Research 314-324 (2014).

Rossi et al., *Retaining the long-survive capacity of Circulating Tumor Cells (CTCs) followed by xeno-transplantation: not only from metastatic cancer of the breast but also of prostate cancer patients,* 1(1) Oncoscience 49-56 (2014).

Sharma et al., *Circulating tumor cell isolation, culture, and downstream molecular analysis,* 36 Biotechnology Advances 1063-1078 (2018).

Shen et al., *Current detection technologies for circulating tumor cells,* Chem. Soc. Rev., The Royal Society of Chemistry (Apr. 10, 2017); Downloaded by Michigan Technological University on Oct. 4, 2017 (19 pages).

Sollier-Christen et al., *VTX-1 Liquid Biopsy System for Fully-Automated and Label-Free Isolation of Circulating Tumor Cells with Automated Enumeration by BioView Platform,* 93A Cytometry 1240-1245 (2018).

Torphy et al., *Circulating Tumor Cells as a Biomarker of Response to Treatment in Patient-Derived Xenograft Mouse Models of Pancreatic Adenocarcinoma,* 9(2):e89474 PLOS One 1-7 (Feb. 2014).

Williams et al., *Generation of Prostate Cancer Patient Derived Xenograft Models from Circulating Tumor Cells,* 104:e53182 Journal of Visualized Experiments 1-6 (Oct. 2015).

Yohe et al., *Review of Clinical Next-Generation Sequencing,* 141 Arch. Pathol. Lab. Med. 1544-1557 (2017).

* cited by examiner

ANIMAL MODEL FOR AMPLIFYING HUMAN OR ANIMAL CIRCULATING TUMOR CELLS

CROSS-REFERENCE TO RELATED APPLICATIONS

This application is a U.S. National Stage Application pursuant to 35 U.S.C. § 371 of International Patent Application PCT/FR2019/052571, filed on Oct. 29, 2019, and published as WO 2020/089560 on May 7, 2020, which claims priority to French Patent Application 1859992, filed on Oct. 29, 2018, all of which are incorporated herein by reference in their entireties for all purposes.

FIELD OF THE INVENTION

The present invention relates to an avian model enabling the amplification of human or animal circulating tumour cells (CTC).

PRIOR ART

CTC are cells that detach from a tumour and which are capable of being displaced to pass into the blood, after having joined the vascular system. These cells can thus migrate to other organs and participate in the development of metastases. These cells thus represent a very attractive target in the monitoring of the evolution and the treatment of cancers, or even in the discovery of novel therapeutics.

The isolation of CTC is not however an easy thing because these cells are very few in number. It is thus necessary to expand them before being able to study them. At present, CTC can be amplified using in vitro or in vivo cultures in murine models (Kowalik A et al., 2017; Drapkin B. J. et al., 2018). In vitro cultures of CTC derived from numerous cancers (lung cancer, prostate cancer, breast cancer, urinary tract cancer, head cancer or neck cancer, etc.) have already been produced, making it possible to conduct high speed preclinical tests of therapeutic regimes, but with limited success because these cultures are too long to be compatible with clinical practice and expose the CTC to phenotype modifications (Pantel K, Alix-Panabières C., 2016).

Short term in vivo cultures have moreover been established in a murine model, from CTC, and after a first step of in vitro expansion when the amount of CTC was too low (Giuliano M et al., 2015; Williams E S et al., 2015; Torphy R J et al., 2014; Rossi E et al., 2013). The direct inoculation of CTC in immunodeficient mice has also been envisaged as a method for amplifying isolated CTC. In highly metastatic small cell lung cancers (SCLC), CTC isolated in patients having a high level of CTC (>400 CTC per 7.5 mL of blood) formed tumours in mice for which the response to chemotherapies with platinum and with Etoposide corresponded to the clinical observations (Hodgkinson, C. L. et al., 2014). These studies open the way to the use of immunodeficient mice as "incubators" of CTC, capable of generating preclinical models adapted to the individual tumours of patients.

However, these models are too expensive to envisage the systematic use thereof. They frequently require having to carry out a prior step of in vitro expansion with the aforementioned drawbacks. Finally, the establishment of these models requires time, which is not always compatible with the observation of the desired effects.

There thus exists a need to find a less expensive in vivo model, but also which gives results more rapidly, and in particular which does not necessitate a prior in vitro expansion phase in order to work on these CTC which are the closest to those present in vivo in patients.

SUMMARY OF THE INVENTION

The present invention relates to an animal model for studying circulating tumour cells constituted of an embryonated bird's egg, preferentially of chicken, comprising human or animal circulating tumour cells (CTC) isolated from a sample of a patient or an animal suffering from cancer, said CTC being grafted at the level of the chorioallantoic membrane (CAM) of an embryonated egg being at a development stage which corresponds to the formation of the CAM at the moment of the graft and equivalent to at least 8 days of development in chickens.

This embryonated egg is an animal model, and more specifically avian model, for amplifying CTC. It also makes it possible to study the effect of different agents on tumorigenesis to select those which have anti-cancer activity and which may consequently represent efficacious therapies, notably for treating the patient or the animal from which the CTC that have been grafted in the embryonated egg are derived. This then makes it possible to administer to the patient a therapeutic agent tested beforehand on cells of his or her own tumour; thus leading to personalised treatment.

The present invention also relates to a method for preparing this embryonated bird's egg model, enabling the amplification of human or animal circulating tumour cells (CTC) derived from a sample of a patient or an animal suffering from cancer, said method comprising the grafting of CTC isolated from said sample at the level of the chorioallantoic membrane (CAM) of an embryonated bird's egg which is at a development stage corresponding to the formation of the CAM and equivalent to at least 8 days of development in chickens.

The present invention also has for subject matter a method for amplifying human or animal circulating tumour cells (CTC) isolated from a sample of a patient or an animal suffering from cancer, comprising the following steps:

a) preparation of an embryonated egg model in accordance with the invention, by grafting CTC isolated from a sample of a patient or an animal suffering from cancer so at the level of the chorioallantoic membrane (CAM) of an embryonated bird's egg which is at a development stage corresponding to the formation of the CAM and equivalent to at least 8 days of development in chickens, b) collection of tumours that develop from CTC which are amplified, and optionally c) recovery of CTC from the tumours collected at step b). Preferably, several grafting rounds may be carried out within the scope of this method, and advantageously two grafting rounds, in order to further optimise the amplification of CTC. It thus involves carrying out a secondary graft, on the CAM of a second embryonated egg, of tumours derived from a first graft of CTC on the CAM of a first embryonated egg.

The present invention also relates to a method for determining the sensitivity of a patient or an animal suffering from cancer to one or more therapeutic agent(s), characterised in that it comprises:

amplification of circulating tumour cells (CTC) derived from a sample of said patient or animal suffering from cancer in accordance with the present invention, by grafting CTC isolated from a sample of a patient or an animal suffering from cancer at the level of the cho-
rioallantoic membrane (CAM) of an embryonated
bird's egg which is at a development stage correspond-
ing to the formation of the CAM and equivalent to at
least 8 days of development in chickens, grafting tumours that have developed in the embryo, at the
level of the chorioallantoic membrane (CAM) of a new
embryonated bird's egg incubated beforehand up to a
development stage corresponding to the formation of
the CAM and equivalent to at least 8 days of develop-
ment in chickens, administration of the therapeutic agent(s) in the embryo-
nated egg at least 12 hours after the graft, study of the effect of the therapeutic agent(s) thereby
administered on the tumorigenesis of tumours that have
developed in this new grafted embryonated egg.

Preferably, this method for determining the sensitivity of
a patient or an animal suffering from cancer to one or more
therapeutic agent(s) further comprises, after the administra-
tion of said agent(s), incubation of the grafted embryonated
egg for at so least 1 hour, and optionally a step of collection
of the tumours that develop from grafted CTC at the end of
the incubation of said new grafted embryonated egg.

The present invention further has for subject matter a
method for monitoring a patient or an animal suffering from
cancer, comprising:

preparation of a first embryonated bird's egg as described
above, with CTC isolated from a sample of said patient
or animal at a time T1, and tumorigenesis study of
tumours that develop in this first embryonated egg, preparation of a second embryonated bird's egg as
described above, with CTC isolated from a sample of
the same patient or animal at a time T2, and tumori-
genesis study of tumours that develop in this second
embryonated egg, comparison of the tumorigenesis of tumours that have
developed in the first and in the second embryonated
egg.

Finally, the present invention has for subject matter a
method for screening therapeutic agents intended for the in
vivo treatment of cancer, comprising:

preparation of an embryonated egg model according to
the method described above, by grafting CTC isolated
from a sample of a patient or an animal suffering from
cancer at the level of the chorioallantoic membrane
(CAM) of an embryonated bird's egg which is at a
development stage corresponding to the formation of
the CAM and equivalent to at least 8 days of develop-
ment in chickens, administration of one or more candidate agents in the
embryonated egg at least 12 hours after the graft, study of the effect of the therapeutic agent(s) thereby
administered on the tumorigenesis of tumours that have
developed in the grafted embryonated egg.

FIGURE CAPTIONS

First grafting round (first group of eggs): CTC isolated
from a sample collected from the patient are grafted in one
egg per patient. Second grafting round (second group of
eggs): the secondary graft enables a new amplification of the
tumours collected in the post-graft eggs.

Figure 3:
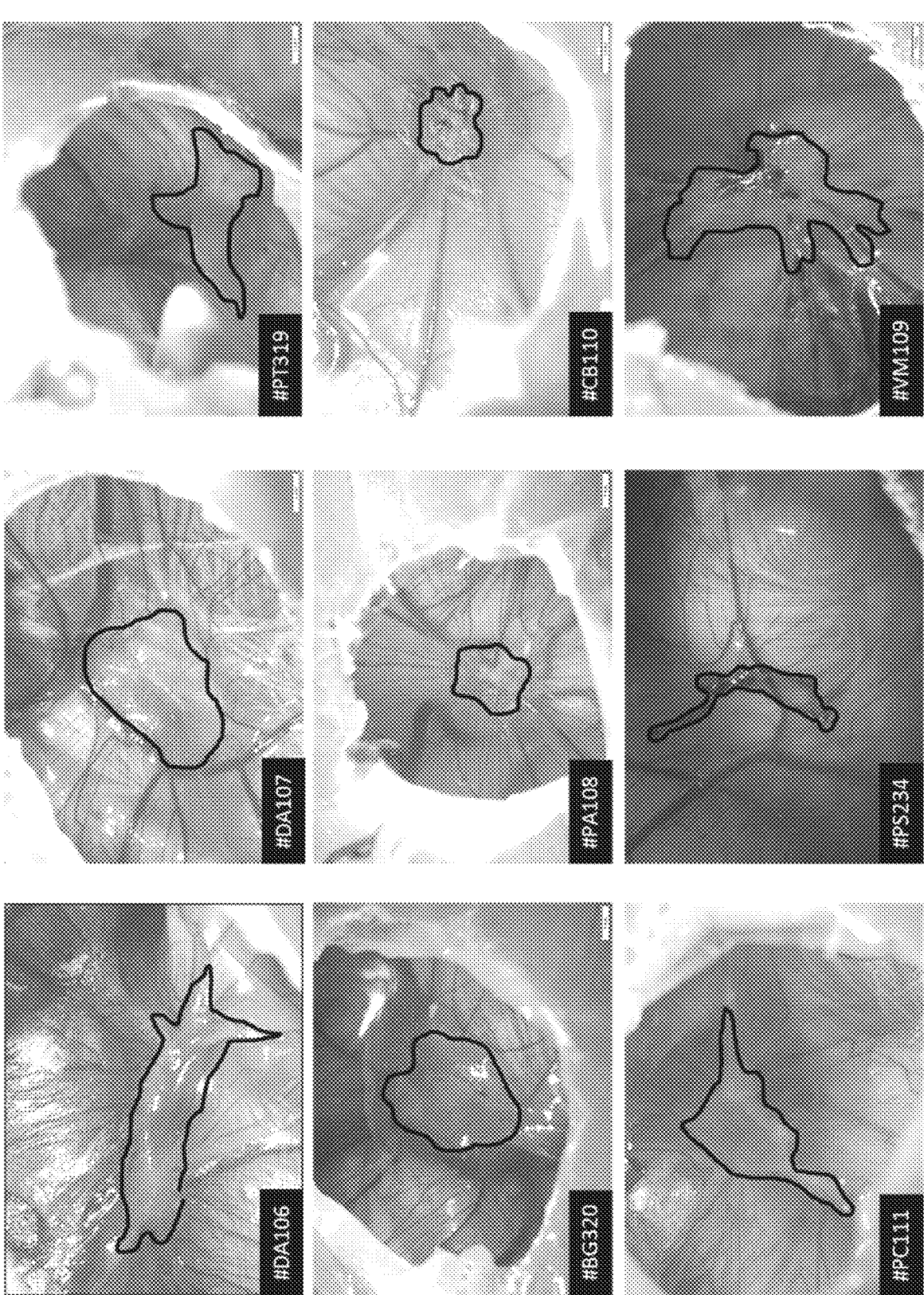

FIG. 3 represents in ovo images of the growth of tumours
obtained by xenografts on CAM at the first round of ampli-
fication of CTC isolated from the blood of patients suffering
from lung cancer, breast cancer, or prostate cancer.

Figure 4:
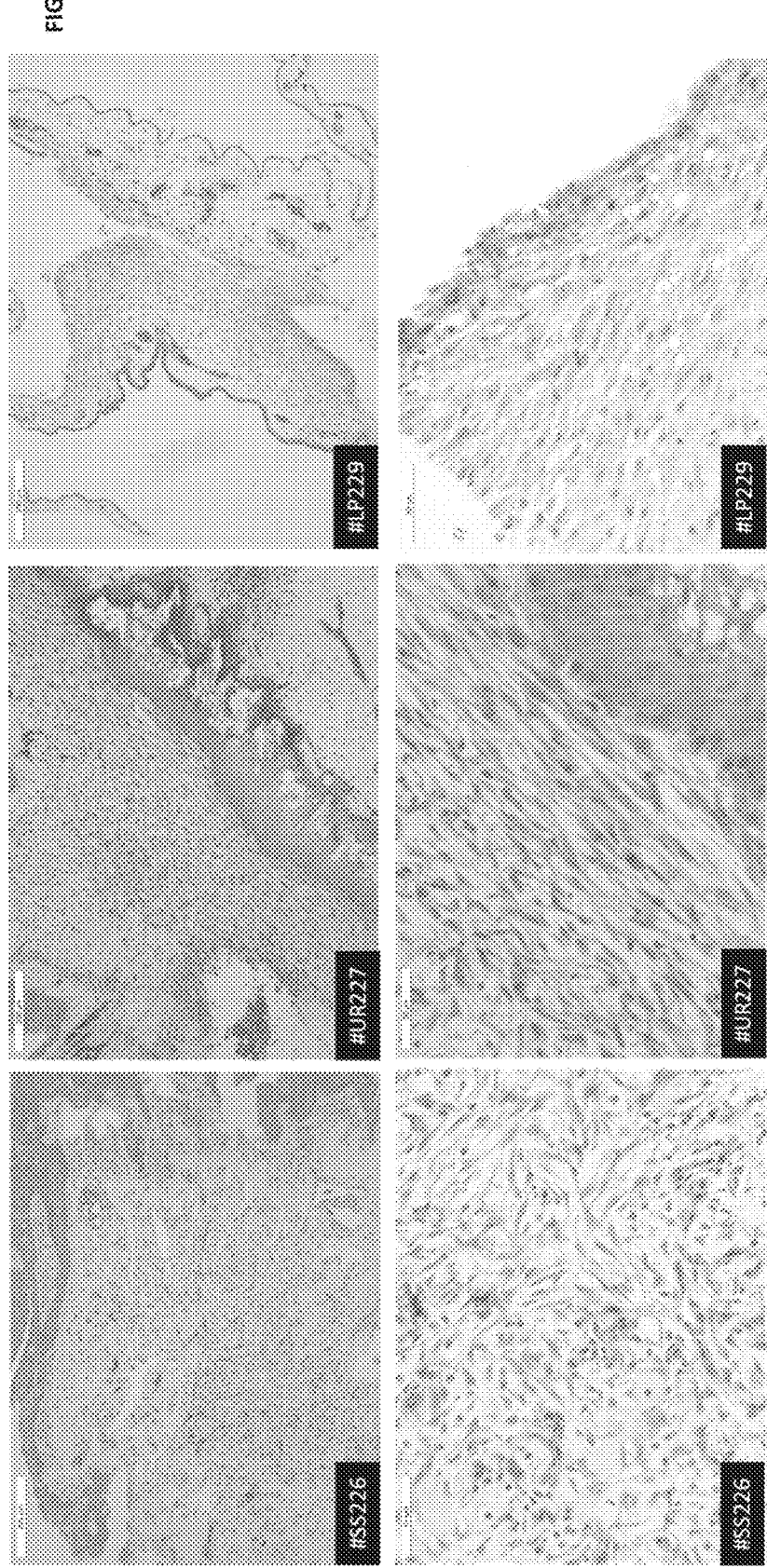

FIG. 4 represents histological sections of tumours derived
from CTC isolated from the blood of patients suffering from
breast cancer, grafted on CAM at the first amplification
round.

FIG. 5 represents the results of genetic analyses of the
human tumour markers TP53 (A) and KRAS (B) on tumours
derived from CTC of patients suffering from lung cancer
(#SH103 and #CM105), grafted on CAM at the first ampli-
fication round.

Figure 6:
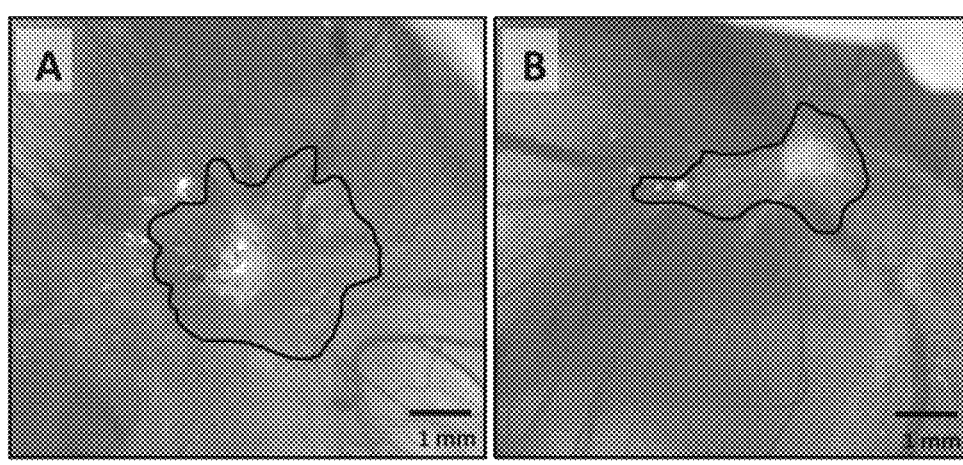

FIG. 6 represents in ovo images of the growth of tumours
derived from CTC isolated from the blood of a patient
suffering from lung cancer, grafted on CAM at the second
amplification round (secondary graft).

FIG. 7 represents in ovo images of tumours obtained from
CTC isolated from the blood of a patient suffering from
prostate cancer following the primary (A) and secondary (B)
graft, as well as the histological analysis of a section of the
tumour (C) demonstrating the amplification of the CTC
grafted in ovo after a secondary graft.

DETAILED DESCRIPTION OF THE INVENTION

The present invention relates to an animal model, in
particular an avian model, for studying circulating tumour
cells constituted of an embryonated bird's egg comprising
human or animal circulating tumour cells (CTC) isolated
from a sample of a patient or an animal suffering from
cancer, said CTC being grafted at the level of the chorioal-
lantoic membrane (CAM) of an embryonated egg being at a
so development stage which corresponds to the formation of
the CAM and equivalent to at least 8 days of development
in chickens at the moment of the graft.

Preferably, the embryonated egg according to the inven-
tion is an egg of a bird of the order Galliformes or Stru-
thioniformes. In particular, it is particularly preferred that
the egg is an egg of gallinaceans, and notably chicken, quail,
turkey, pheasant, peacock, guinea fowl or other farmyard
birds. It may also be an ostrich egg. Advantageously, the
embryonated egg according to the present invention is a
chicken egg (Gallus gallus).

Within the scope of the present invention, the term
"embryonated egg" designates a fertilised bird's egg in
which the embryo can develop under suitable conditions, in
particular in an incubator at a temperature of 37° C. to 38°
C. Under these conditions, the incubation time necessary to
end up with the hatching of the egg is 21 days for chicken.

The development stages taught here are defined as a
function of the post-fertilisation incubation time of the eggs,
in particular the incubation time under suitable conditions
such as defined above. "Graft at the level of the CAM" is
taken to designate the administration by apposition or injec-
tion on the CAM, whether this is the upper CAM or the
lower CAM.

The embryonated egg model according to the invention
has cells derived from two different organisms or xeno-
grafts: the cells of the "host" or "receiver" bird and the CTC
grafted in the egg which are derived from a human or animal
organism of a species different from that of the "receiver"
bird. In a particularly preferred manner, the CTC grafted in
the embryonated bird's egg are human cells. These grafted CTC are then going to develop in the embryo while forming one or more solid tumours and/or while being displaced in the egg.

By definition, the "graft at the level of the CAM" takes place once the CAM has been formed and at a stage equivalent to at least 8 days of development in chickens, under normal and standard growth conditions. If the bird used is a chicken, this stage corresponds to at least 8 days of development. The number of days of development being able to vary from one species to the other, the graft make take place after varying days of development. For example, a development stage of at least 8 days in chickens corresponds to a development stage of at least 6.5 days in quail.

"Sample of patient or animal suffering from cancer" should be understood to mean any sample derived from a human or an animal suffering from cancer and which contains CTC. Preferably, said sample is selected from total blood or from biological fluids capable of containing CTC such as pleural effusion fluid, ascites and cerebrospinal fluid (CSF), and preferably total blood. Thus, the CTC grafted in the embryonated egg may come from any type of cancer producing CTC in the blood or this type of fluid, and in particular metastatic cancers. According to a preferred embodiment of the present invention, the patient or the animal from which the CTC grafted in the embryonated egg are isolated is suffering from at least one cancer selected from lung cancer, prostate cancer, breast cancer, colorectal cancer.

Advantageously, the embryonated egg model according to the invention is a chicken egg in which human CTC have been grafted at the level of the CAM and after at least 8 days of development.

It is understood that the embryo grafted according to the present invention does not have the vocation to hatch and is consequently not intended to create an adult organism. It is for this reason that the embryo grafted according to the present invention is a model intended to receive CTC for the time of their amplification, not extending to hatching, which corresponds to 21 days of development in chickens. Whatever the case, the bird embryo according to the invention will be sacrificed, according to the ethical rules in force, before hatching and after the grafted CTC will have led to the development of one or more tumours in the egg.

Such a model makes it possible at one and the same time to amplify CTC, notably by the development of tumours from these CTC on which it will be possible to test the anti-cancer activity of different agents, which are either known to have such an activity or candidates to determine if they have such an activity. The comparative efficacy of several therapeutic agents could also be tested, in order to determine the most promising therapy for treating the patient from whom the grafted CTC are derived.

According to a second aspect, the present invention relates to a method for preparing the embryonated bird's egg model described above, enabling the amplification of human or animal circulating tumour cells (CTC) isolated from a sample of a patient or an animal suffering from cancer, said method comprising the grafting of CTC isolated from said sample at the level of the chorioallantoic membrane (CAM) of an embryonated bird's egg that is at a development stage corresponding to the formation of the CAM and equivalent to at least 8 days of development in chickens.

Those skilled in the art will know how to determine the moment to carry out the grafting of CTC, as a function of the species of bird used, that is to say the minimum number of days of incubation or development of the embryonated egg to arrive at formation of the CAM and at a development stage equivalent to at least 8 days of development in chickens. For example, in chickens, the graft could take place from 8 days of development, and in quail from 6.5 days of development.

According to a preferred embodiment, the embryonated egg has been, prior to the graft, incubated up to a development stage corresponding to the formation of the CAM and equivalent to at least 9 or in an even more preferred manner at least 9.5 days of development in chickens.

The incubations are carried out under suitable conditions, that is to say conditions that enable normal development of the embryonated egg, notably at a temperature comprised between 37° C. and 39° C., and preferably 38° C., or even 38.5° C.

The grafting of CTC may be carried out at any place of the CAM, upper or lower, preferably at the level of the upper CAM. Any method well known to those skilled in the art could be used for this graft and, in particular, it is possible to use the grafting technique referenced by Crespo P. & Casar B, 2016.

According to a particular embodiment, the amount of grafted CTC goes from around 5 to around 5000 CTC, in a preferred manner from around 5 to around 2500 CTC and in an even more preferred manner from around 5 to around 1000 CTC.

According to a preferred embodiment, the CTC used are frozen after isolation from the sample of the patient or animal suffering from cancer and before the graft in the embryonated egg.

For the graft at the level of the CAM, the CTC are isolated from the sample of the patient or animal suffering from cancer, by any one of the methods well known to those skilled in the art. Thus, the CTC are isolated by purifying them from the other cells present in the sample derived from the patient or animal suffering from cancer, and in particular by separating them from immune cells present in the sample.

The methods for isolating CTC may be based on different principles making it possible to separate them from the other constituents of a sample, and consequently to carry out CTC enrichment. A large number of different methods have notably been described by Zheyu Shen et al., 2017. They make it possible to end up with a so-called "negative" enrichment when the objective is to capture the untargeted cells and to elute CTC, or to a so-called "positive" enrichment when the objective is to capture CTC and to elute the untargeted cells of the sample.

Among these methods, it is possible to cite separation methods by filtration, and in particular by vertical filtration such as for example the ISET (Isolation by SizE of Tumor cell) technology sold by the Rarecells SAS Company and notably described by Han Wei Hou et al., 2013.

Certain methods may resort to a marking step, such as the CellSearch method (Kagan M, et al., 2002) which is based on an immuno-selection of CTC using nanoparticles of ferrofluid with antibodies that target a specific epithelial cell adhesion marker (EpCAM). The CTC are thus separated magnetically from the major part of the other blood cells.

Other methods based on the use of microfluidic systems, which rely on separation as a function of different parameters such as the size, the shape, the density, the deformability of the cells, may also be used. Among these may notably be cited the VTX-1 method such as described by Sollier-Christen et al., 2018, a microfluidic method (CTC-chips) based on the capture of the tumour cells expressing the EpCam molecule using microspots coated with anti-EpCam antibodies, which is notably described by Nagrath S et al., 2007, the RosetteSep technology of the Stemcells Company which uses a mixture of antibodies (CD45, CD66b and glycophorin A) coupled to magnetic beads, targeting red blood cells and white blood cells or instead the ClearCell Fx1 method developed by the Biolidics Company (formerly ClearBridge), which is in particular described by Laget S et al., 2017 and which is particularly advantageous.

According to a particular embodiment, the method for preparing the embryonated bird's egg model according to the invention further comprises a step of incubation of the embryonated egg once grafted for at least 12 hours, preferably at least 24 hours, in an even more preferred manner at least 48 hours after the graft, before being used. Preferably, the embryonated egg once grafted is incubated at the most for 20 days, and in particular up to 18 days, with reference to the stages of development of a chicken embryo.

According to a third aspect, the present invention relates to a method for amplifying human or animal circulating tumour cells (CTC) isolated from a sample of a patient or an animal suffering from cancer, comprising the following steps:

a) grafting CTC isolated from a sample of a patient or an animal suffering from cancer at the level of the chorioallantoic membrane (CAM) of an embryonated bird's egg which is at a development stage corresponding to the formation of the CAM and equivalent to at least 8 days of development in chickens, as described above, b) collection of tumours that develop from the CTC that are amplified, and optionally c) recovery of CTC from the tumours collected at step b).

The inventors have demonstrated, in a surprising manner, that CTC and in particular CTC of human origin may be amplified in an embryonated bird's egg model, which makes it possible to obtain them in sufficient amounts to study them, but also to use them to lead to the identification of novel treatments or to select that which promises to be the most efficacious in an individualised manner.

According to a preferred embodiment of the method for amplifying human or animal circulating tumour cells (CTC) described above, it is possible to graft once again the CTC that will have been amplified by carrying out for example several grafting and collection rounds (the term secondary graft is employed for two grafting rounds), so and this is so in order to further improve the amplification of CTC. Thus, the method may comprise the following steps:

a) grafting CTC isolated from a sample of a patient or an animal suffering from cancer at the level of the chorioallantoic membrane (CAM) of an embryonated bird's egg that is at a development stage corresponding to the formation of the CAM and equivalent to at least 8 days of development in chickens, b) collection of tumours that develop from CTC that are amplified, b1) grafting the tumours collected at step b) at the level of the chorioallantoic membrane (CAM) of a second embryonated bird's egg incubated beforehand up to a development stage corresponding to the formation of the CAM and equivalent to at least 8 days of development in chickens, b2) optionally incubation of this second embryonated egg thereby grafted for at least 12 hours, b3) collection of tumours that develop from the tumours grafted at step b1), and optionally, c) recovery of CTC from the tumours collected at step b3).

According to a particular embodiment, the method for amplifying human or animal circulating tumour cells (CTC) described above further comprises a step of incubating the embryonated egg once grafted for at least 12 hours, preferably at least 24 hours, in an even more preferred manner at least 48 hours after the graft, before carrying out the collection of tumours derived from grafted CTC. Preferably, the embryonated egg once grafted is incubated at the most for 20 days, and in particular up to 18 days, with reference to the stages of development of a chicken embryo.

The present invention thus also relates to a method for determining the sensitivity of a patient or an animal suffering from cancer to one or more therapeutic agent(s), characterised in that it comprises:

amplification of CTC isolated from a sample of a patient or an animal suffering from cancer in an embryonated bird's egg, as described above, grafting the tumours thereby collected at the level of the chorioallantoic membrane (CAM) of a new embryonated bird's egg incubated beforehand up to a development stage corresponding to the formation of the CAM and equivalent to at least 8 days of development in chickens, administration of the therapeutic agent(s) in the embryonated egg at least 12 hours after the graft, study of the effect of the therapeutic agent(s) thereby administered on the tumorigenesis of tumours that have developed in this new grafted embryonated egg.

"Therapeutic agent" is taken to designate any chemical or biological molecule or compound, nanostructure, physical methods or combinations thereof having an anti-tumour action, and in particular potentially efficacious for treating the type of cancer that has developed from tumorous cells grafted in the embryonated egg.

Such compounds may be chemical molecules such as chemotherapies, biological compounds such as antibodies, therapeutic cells such as CART, physical agents such as irradiations, intercalating agents such as for example Irinotecan, signal pathway inhibitors of tyrosine kinase such as for example Sunitinib, anti-hormonals such as for example Tamoxifen, immunoregulators such as for example Ketruda, membrane receptor inhibitors such as for example Trastuzumab, etc.

Within the scope of the present invention, the terms tumour and cancer are used indifferently, and with the same signification, to define a proliferation of malignant cells. The same is true for the use of the terms antitumoral and anticancer.

In particular, since the grafted CTC are isolated from a sample of patient or animal suffering from cancer, the fact of testing several therapeutic agents makes it possible to be able to select that which is the most promising for the treatment of the tumour in this patient. It is thus that, according to a preferred embodiment of the present invention, the embryonated bird's egg grafted with CTC is used to determine the agent that has the best anti-cancer activity among the different agents tested.

The embryonated bird's egg grafted with CTC may also be used according to the present invention to test the anti-cancer efficacy of combinations of therapeutic agents compared to the effect obtained with each of the agents tested independently.

Within the scope of the use of this embryonated egg, it is also possible to determine, or even to quantify, the toxicity of the therapeutic agent(s) tested, both on the tumours that have developed from grafted CTC and on the embryo as a whole. Consequently, another subject matter of the present invention relates to the use of an embryonated bird's egg grafted with CTC isolated from a sample of a patient or an animal suffering from cancer to quantify the toxicity of one or more therapeutic agent(s) on the tumour and/or on the embryo as a whole.

The step of administration of the therapeutic agent(s) in the embryonated egg may be carried out in different ways by techniques well known to those skilled in the art. The administration may notably be carried out by apposition or injection at the level of the CAM, by intra-tumoral injection, by injection into the embryonic or extra-embryonic structures of the egg.

The administration of the therapeutic agent(s) is carried out at least 12 h after the grafting of CTC, preferably at least 24 h, or in an even more preferred manner at least 48 h after the graft, that is to say 1 to 2 days after the graft. The therapeutic agent(s) may also be administered according to different regimes in terms of duration, but also number of administrations, such as for example every two days, or every day, or twice a day, or a single injection, and this up to the final day of incubation of the egg. These choices will be determined as a function of the agent administered.

According to a preferred embodiment, the method for determining the sensitivity of a patient or an animal suffering from cancer to one or more therapeutic agent(s) according to the invention further comprises the incubation of the embryonated egg once grafted for at least 1 hour, after administration of the therapeutic agent(s) in the grafted embryonated egg before studying the effect on tumorigenesis. Advantageously, the incubation is carried out for at least 4 days and at the most 12 days after administration, to correspond to a development stage of the embryo of 21 days maximum, and advantageously 18 days of development. According to a particular embodiment, the method for determining the sensitivity of a patient or an animal suffering from cancer to one or more therapeutic agent(s) according to the invention further comprises the collection of tumours that develop from the grafted CTC at the end of the incubation of said embryonated egg after administration of the therapeutic agent(s) that have been administered, and notably by microdissection. The study of the effect of the therapeutic agent(s) thereby administered on tumorigenesis may take several complementary approaches, in particular after collection of tumours that have developed in the grafted embryonated egg. It may notably comprise the analysis of parameters such as tumour growth, metastatic invasion, angiogenesis, neo-angiogenesis, inflammation and/or tumour immune infiltration, toxicity on the tumour and/or on the embryo as a whole.

The tumours may thus be subjected to analyses for measuring and/or analysing these different parameters, such as tumoral weight and/or volume for studying tumour growth, the expression of different specific markers for studying metastatic invasion such as the amplification of the Alu sequence by quantitative PCR for human metastasis, the number of vessels in the tumour for angiogenesis and neo-angiogenesis, the quantification of interleukins for inflammation and/or the quantification, notably by rtQPCR, of markers such as CD3, CD8, CD4, CD45 and CD56 to assess tumour immune infiltration, weight, and histological analyses to evaluate toxicity on the tumour.

The study of metastatic invasion may be carried out on the lower CAM, easily accessible, but it may also be carried out in any target organ within the embryo, notably as a function of the type of cancer and known data on the associated metastasis phenomenon.

Inflammation and/or tumour immune infiltration may notably be studied by the analysis of the expression of different markers, such as CD3 (T lymphocyte membrane marker), CD4 (regulatory T lymphocyte, monocyte and macrophage membrane marker), CD8 (cytotoxic T lymphocyte marker), CD45 (leukocyte membrane marker), CD56 (NK cell marker), etc. Pairs of specific oligonucleotides of these markers will be able to be developed, in order to avoid cross breeding between species.

By extension, it is also possible to monitor inflammation and infiltration of cells of the immune system in sites of metastases.

The combined analysis of all these factors, well known to those skilled in the art, makes it possible to determine the sensitivity of the patient or the animal suffering from cancer from which the grafted CTC are derived to the therapeutic agent(s) administered in the embryo. These parameters notably form an integral part of the decision tree used by clinicians to decide the therapeutic management to adopt in patients suffering from cancer.

Within the scope of all the methods according to the invention that comprise the effect of therapeutic agent(s) on tumorigenesis, these parameters are preferentially assessed by comparison after administration of the therapeutic agent(s) in the embryonated egg once grafted compared to those determined in another embryonated egg of the same bird grafted beforehand according to the same method with the same CTC but in which no therapeutic agent has been administered. Similarly, when the effect of several therapeutic agents is studied, the effect will preferentially be assessed by comparison of the parameters after administration of the combination of therapeutic agents in the embryonated egg once grafted compared to those determined in one or more other embryonated egg(s) of the same bird grafted beforehand according to the same method with the same CTCs but in which each of the therapeutic agents has been administered individually.

According to another aspect, the invention also pertains to a method for monitoring a patient or an animal suffering from cancer, comprising:

preparation of a first embryonated bird's egg as described above with CTC isolated from a sample of said patient or animal at a time T1, and tumorigenesis study of tumours that develop in this first embryonated egg, preparation of a second embryonated bird's egg as described above with CTC so isolated from a sample of the same patient or animal at a time T2, and tumorigenesis study of tumours that develop in this second embryonated egg, comparison of the tumorigenesis of tumours that have developed in the first and in the second embryonated eggs.

The present invention also has for subject matter a method for screening therapeutic agents intended for the in vivo treatment of cancer, comprising:

grafting circulating tumour cells isolated from a sample of a patient or an animal suffering from cancer at the level of the CAM of an embryonated bird's egg incubated beforehand up to a development stage corresponding to the formation of the CAM and equivalent to at least 8 days of development in chickens, administration of one or more candidate agents in the embryonated egg, at least 12 hours after the graft, study of the effect of the therapeutic agent(s) thereby administered on the tumorigenesis of tumours that have developed in the grafted embryonated egg. "Candidate therapeutic agent" is taken to mean a chemical or biologic therapeutic agent such as defined above and capable of having anti-cancer activity, and in particular potentially efficacious for treating the type of cancer that has developed from tumorous cells grafted in the embryonated egg. The screening method according to the present invention makes it possible to determine if a candidate therapeutic agent has anti-cancer activity or not, and if it has anti-metastasis activity.

All the preferences and precisions mentioned above within the scope of the different methods also apply to the monitoring and screening methods according to the present invention.

EXAMPLES

The invention is illustrated hereafter by the use of an embryonated chicken's egg to amplify human CTC.

Preparation of CTC

The CTC grafted in the embryonated eggs are isolated by filtration based on the size of the cells according to the ISET method (Han Wei Hou et al., 2013) or by microfluidic system according to the ClearCell method (Laget S et al., 2017) from blood samples of patients suffering from lung cancer, breast cancer, or prostate cancer in metastasis phase. The CTC thereby obtained are stored frozen, and thawed just before the graft.

Induction of Tumours

Fertilised eggs of White Leghorn hens are incubated in the supine position for 9 to 10 days at 37.5° C. with a relative humidity of 40%. After this incubation period (E9 or E10), the eggs are prepared to receive the graft. They are opened while preserving the integrity of the CAM, which is lowered by making a small hole through the shell. Then a window of around 1 cm² is cut above the CAM. The CTC (5 to 2500 cells) are grafted by apposition on the CAM, then the eggs are once again incubated at 37.5° C. and 40% humidity. After the graft, in ovo tumours develop on the upper CAM. The eggs are observed every 48 h minimum to monitor the development thereof.

Figure 1:
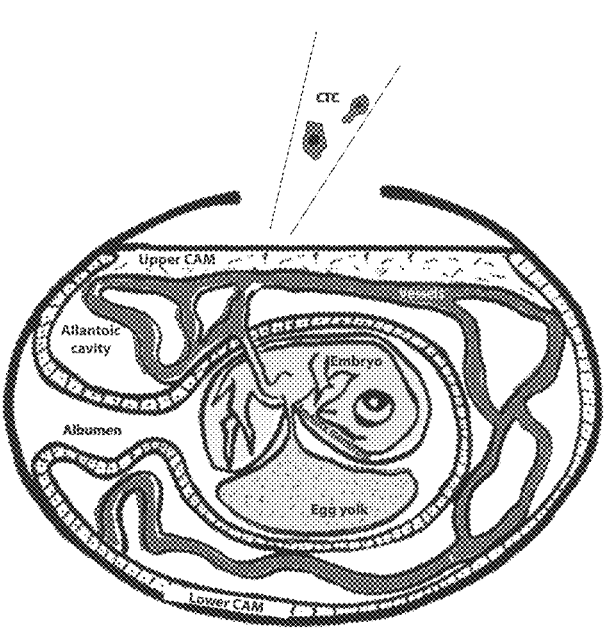
FIG. 1 represents a diagram of the embryonated egg
model with the CTC graft site on the upper CAM.

A diagram of an embryonated egg with the CTC graft site on the upper CAM is represented in FIG. 1. An example of experimental regime is represented in FIG. 2.

At day 18 of development (E18), the upper part of the CAM is removed, washed in saline phosphate buffer then transferred directly into paraformaldehyde (PFA) for fixation for 48 hours. The tumours are next carefully extracted from normal CAM tissue.

Figure 2:
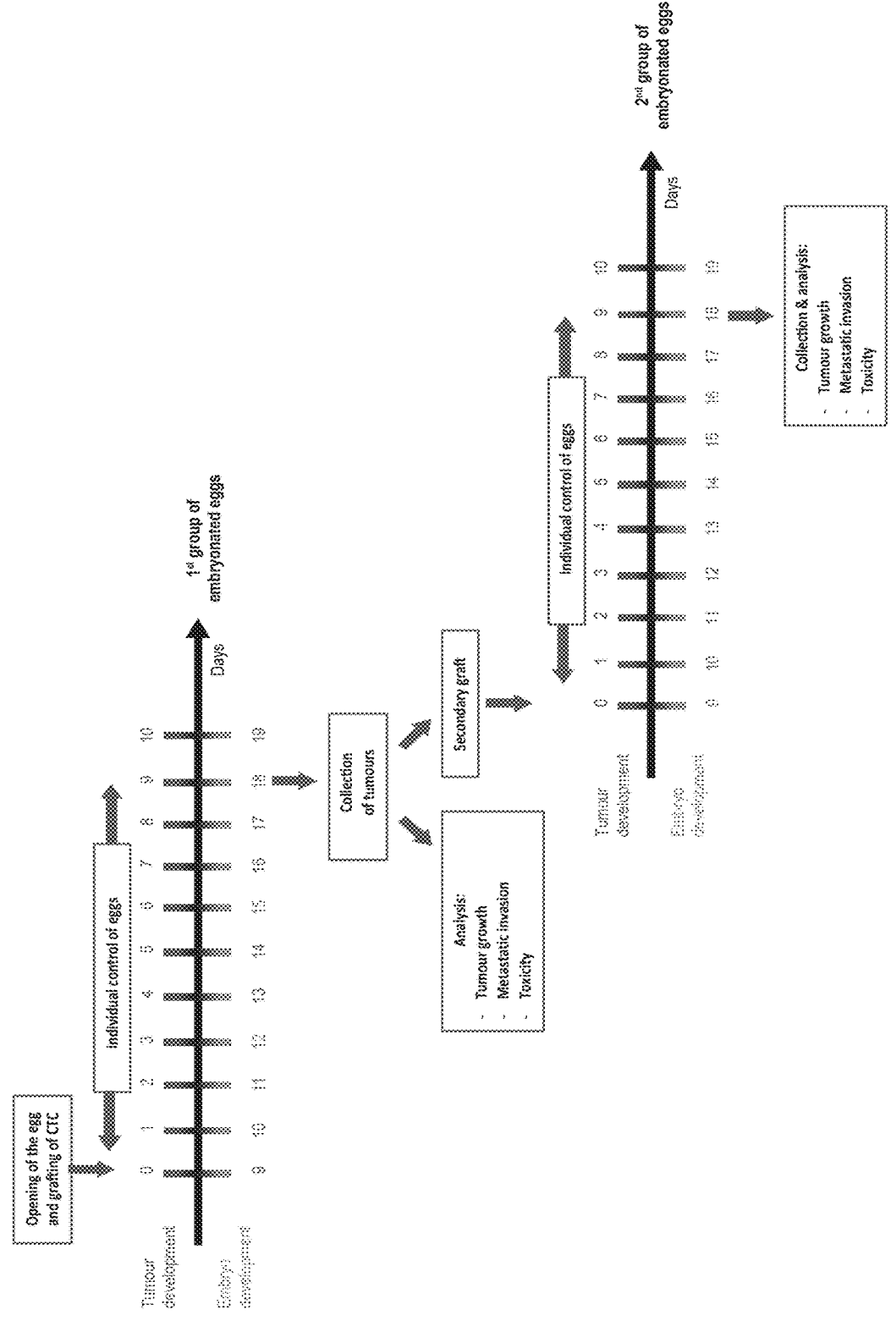
FIG. 2 represents a possible experimental regime for
carrying out the invention.

The tumours collected are next analysed, and notably:
  weighed to study tumour growth (FIG. 2, first round);
  used for histological or genetic analyses (metastases for example) (FIG. 2, first round);
  used for a secondary graft in a new batch of embryonated eggs at 9 days of development for amplification (FIG. 2, second round). This step may be repeated as many times as necessary (with regular control of the phenotype).

Secondary Grafts

After 9 days of growth of the grafted CTC, the tumours that have developed are collected and prepared for the carrying out of a secondary graft. The tumour is cut into small pieces and each piece is grafted in the CAM of a new egg in order to obtain a strong amplification of CTC.

Analysis of Metastases

An analysis of metastases may be carried out either on a portion of the lower CAM (opposite the grafting site) or on embryonic tissues collected at the same time as the tumour and stored in a suitable manner. After extraction of total genomic DNA, the detection of human cells in these samples may be performed by qPCR using specific primers of human Alu sequences (multi-copy sequences well conserved in humans).

Results

The experimental design described above was applied with CTC isolated from the blood of patients suffering from lung cancer (#DA106, #DA107, #PA108, #CB110, #PC111, #VM109, #SH103, #CM105), CTC isolated from the blood of patients suffering from breast cancer (#PS234, #SS226, #UR227, #LP229), CTC isolated from the blood of patients suffering from prostate cancer (#PT319, #BG320).

After 9 days on CAM (E18), all the samples of patient CTC were grafted with success on the CAM and presented a development of tumours. In ovo images of the growth of tumours after a first amplification round are grouped together in FIG. 3.

Histological analyses by Haematoxylin/Eosin coloration were carried out on the tumours collected at the first amplification round and derived from CTC isolated from blood of the patient suffering from breast cancer (#PS234), then grafted onto the upper CAM.

The results are grouped together in FIG. 4, which shows the presence of malignant tumour proliferation.

Finally, analyses of genetic mutations were carried out by high speed sequencing according to the "Next Generation Sequencing" (NGS) method referenced in 2017 in the review of Yohe S & Thyagarajan B. with the human tumour markers TP53 (Mogi A & Kuwano H 2011) and KRAS (Gou L Y et al., 2015) on genomic DNA extracted from tumours collected at the first amplification round and derived from CTC isolated from the blood of patients suffering from lung cancer. The extraction of DNA was carried out according to the method of the GeneJET FFPE DNA Purification Kit sold by ThermoFisher.

Figure 5A:
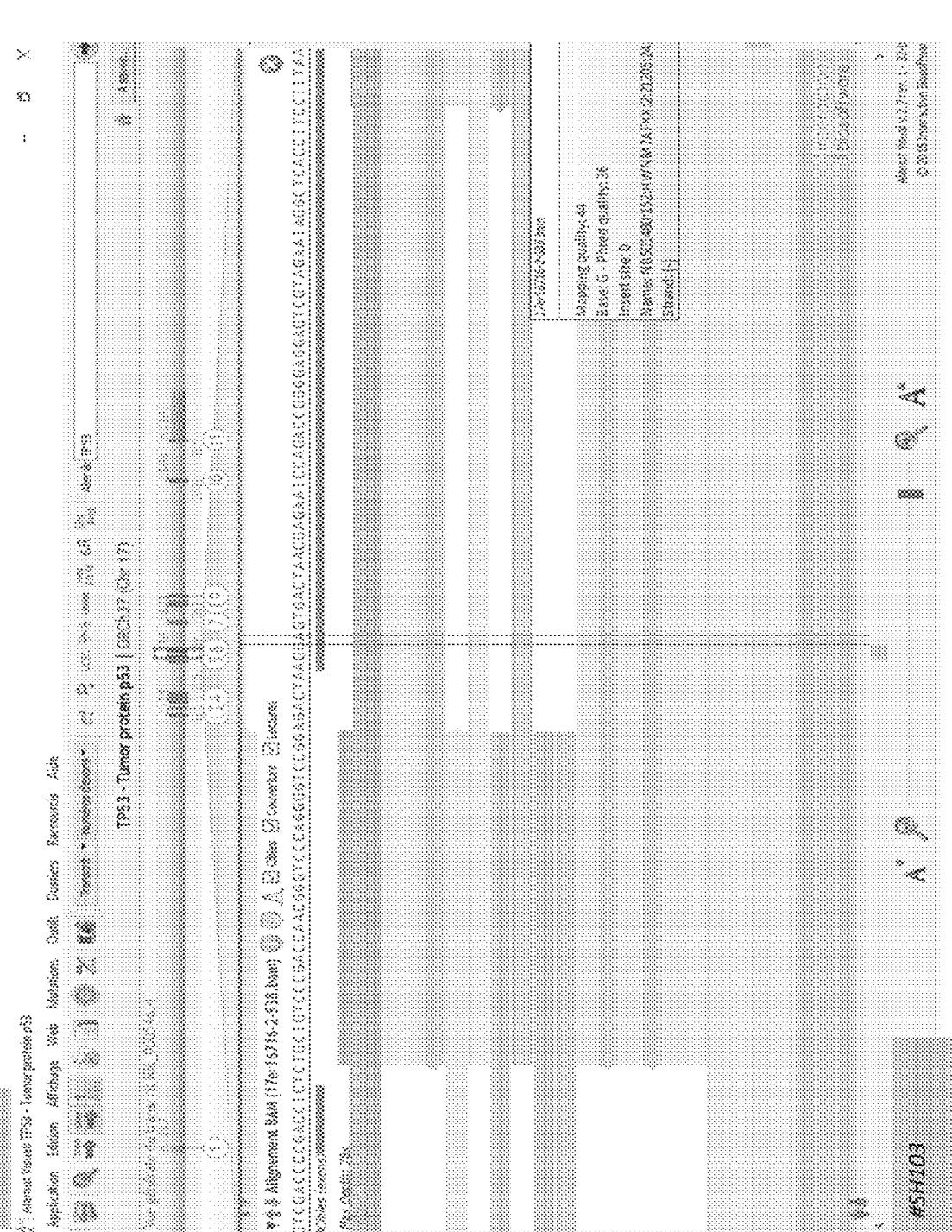
Figure 5B:
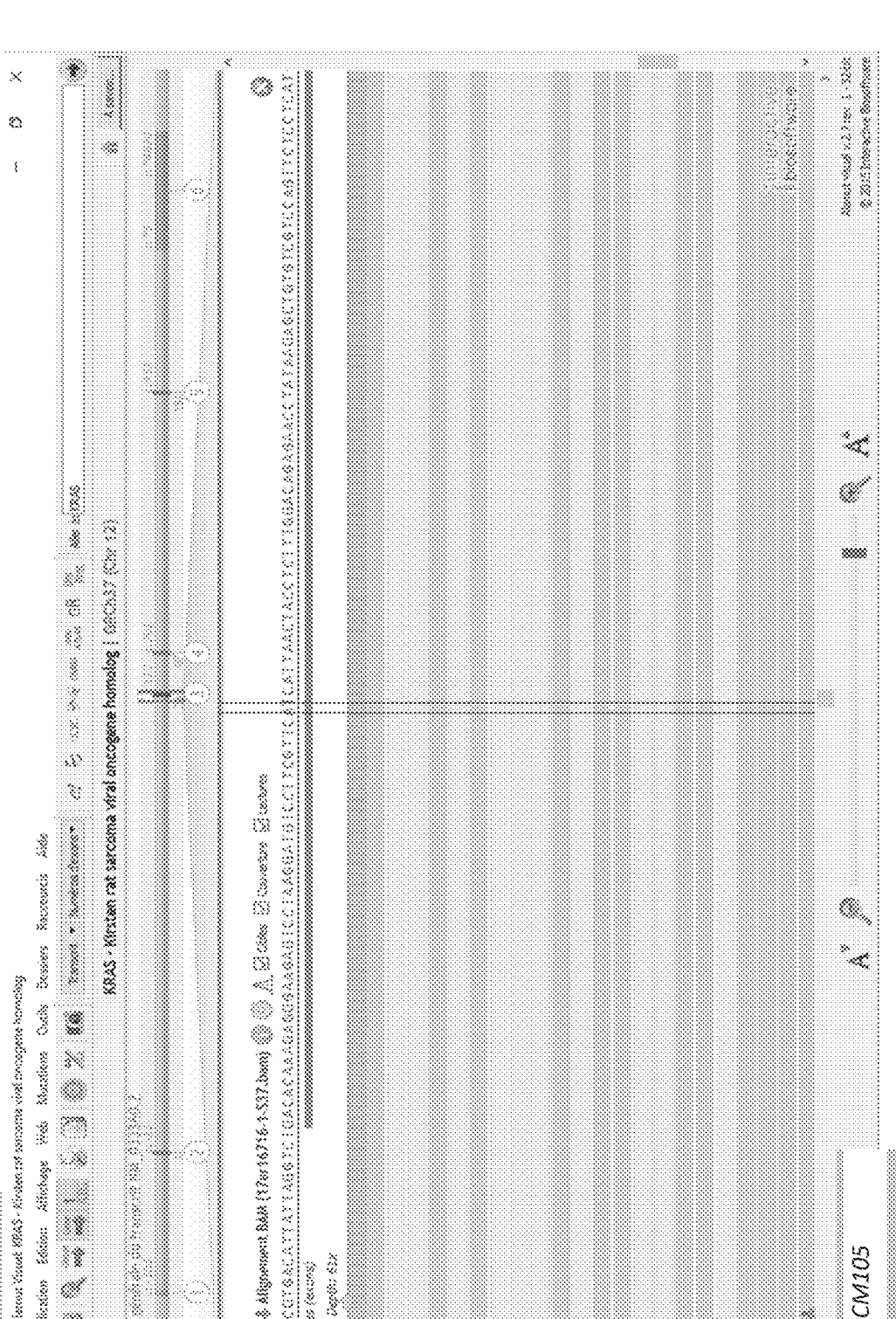

The results are grouped together in FIG. 5, which shows the presence of mutations of the human tumour markers TP53 (FIG. 5A) and KRAS (FIG. 5B) in two distinct tumours derived from a first graft of CTC of patients suffering from lung cancer (#SH103 and #CM105).

The tumours derived from a first graft of CTC isolated from the blood of a patient suffering from lung cancer were collected at E18, cut up then once again grafted onto the CAM of a second group of embryonated eggs. The in ovo images of growth of tumours collected at E18 after a second amplification round are grouped together in FIG. 6 (A and B correspond to in ovo images of tumours on CAM derived from two distinct secondary grafts).

The tumours derived from a first graft of CTC isolated from the blood of a patient suffering from prostate cancer (ClearCell Fx1 microfluidic method) were collected at E18, cut up then once again grafted on the CAM of a second group of embryonated eggs. The in ovo images of growth of tumours are grouped together in FIG. 7. Image A represents the tumour obtained in ovo from CTC following the primary graft. The two sites of tumour development are shown by arrows. Image B corresponds to that of an in ovo tumour on CAM derived from a secondary graft, produced from the tumour shown in A. Image C corresponds to the histological analysis of a section of the tumour represented in B, showing on the one hand the tissue of the CAM, and on the other hand tumoral tissue.

CONCLUSIONS

The results described above show that the use of an avian embryonated egg model enables the in ovo amplification of CTC isolated from samples of patients, in a quicker and less expensive manner compared to the murine model of the prior art. The present invention thus makes it possible to constitute rapidly biobanks of CTC, which may next be used for efficacy tests of anti-cancer therapies, for monitoring and screening novel agents capable of being able to give rise to efficacious and personalised treatments.

REFERENCES

Kowalik A et al. Current approaches for avoiding the limitations of circulating tumor cells detection methods and treatment of patients with solid tumors. Translational Res. 2017. A review article, Vol 185: 58-84;

Drapkin B. J. et al. Genomic and Functional Fidelity of small cell lung cancer Patient-Derived Xenografts. Cancer Discov. 2018 May; 8(5):600-615.

Pantel K, Alix-Panabières C. Functional Studies on Viable Circulating Tumor Cells. Clin Chem. 2016 February; 62(2):328-34.

Giuliano M, Herrera S, Christiny P, Shaw C, Creighton C J, Mitchell T, Bhat R, Zhang X, Mao S, Dobrolecki L E, Al-rawi A, Chen F, Veneziani B M, Zhang X H, Hilsenbeck S G, Contreras A, Gutierrez C, Jeselsohn R M, Rimawi M F, Osborne C K, Lewis M T, Schiff R, Trivedi M V. Circulating and disseminated tumor cells from breast cancer patient-derived xenograft-bearing mice as a novel model to study metastasis. Breast Cancer Res. 2015 Jan. 9; 17:3.

Williams E S, Rodriquez-Bravo V, Chippada-Venkata U, De la Iglesia-Vicente J, Gong Y, Galsky M, Oh W, Cordon-Cardo C, Domingo-Domenech J. Generation of Prostate Cancer Patient Derived Xenograft Models from Circulating Tumor Cells. J Vis Exp. 2015 Oct. 20; (105):53182.

Torphy R J, Tignanelli C J, Kamande J W, Moffitt R A, Herrera Loeza S G, Soper S A, Yeh J J. Circulating tumor cells as a biomarker of response to treatment in patient-derived xenograft mouse models of pancreatic adenocarcinoma. PLoS One. 2014 Feb. 19; 9(2)

Rossi E, Rugge M, Facchinetti A, Pizzi M, Nardo G, Barbieri V, Manicone M, De Faveri S, Chiar a Scaini M, Basso U, Amadori A, Zamarchi R. Retaining the long-survive capacity of Circulating Tumor Cells (CTCs) followed by xeno-transplantation: not only from metastatic cancer of the breast but also of prostate cancer patients. Oncoscience. 2013 Dec. 31; 1(1):49-56

Hodgkinson, C. L., Morrow, C. J., Li, Y., Metcalf, R. L., Rothwell, D. G., Trapani, F., Polanski, R., Burt, D. J., Simpson, K. L., Morris, K., Pepper, S. D., Nonaka, D., Greystoke, A., Kelly, P., Bola, B., Krebs, M. G., Antonello, J., Ayub, M., Faulkner, S., Priest, L., Carter, L., Tate, C., Miller, C. J., Blackhall, F., Brady, G., and Dive, C. (2014). Tumorigenicity and genetic profiling of circulating tumor cells in small-cell lung cancer. Nat Med 20, 897-903.

Crespo P. & Casar B.; Bio-protocol, Vol. 6, Iss 20, Oct. 20, 2016; Chick Embryo Chorioallantoic Membrane as an in vivo Model to Study Metastasis Han Wei Hou et al. Scientific Reports 3, Article number: 1259 (2013)

Laget S et al. PloS one, 2017 Jan. 6; 12(1):e0169427.

Yohe S and Thyagarajan B. Arch Pathol Lab Med. 2017 November; 141(11):1544-1557. Review of Clinical Next-Generation Sequencing Mogi A and Kuwano H; J Biomed Biotechnol. 2011; 2011: 583929. TP53 mutations in nonsmall cell lung cancer.

Gou L Y et al.; Cancer. 2015 Sep. 1; 121 Suppl 17:3069-79. Differences in driver genes between smoking-related and non-smoking-related lung cancer in the Chinese population.

Zheyu Shen et al., Chem Soc Rev, 2017 Apr. 18; 46(8): 2038-2056. Current Detection Technologies of Circulating Tumor Cells.

Sollier-Christen et al., Journal of Quantitative Cell Science, Cytometry Part A, 2018, 93A: 1240-1245.

Kagan M, Howard D, Bendele T, et al., A sample preparation and analysis system for identification of circulating tumor cells. *J Clin Ligand Assay* 2002; 25:104-10.

Nagrath S[1], Sequist L V, Maheswaran S, Bell D W, Irimia D, Ulkus L, Smith M R, Kwak E L, Digumarthy S, Muzikansky A, Ryan P, Balis U J, Tompkins R G, Haber D A, Toner M; Nature. 2007 Dec. 20; 450(7173):1235-9.

The invention claimed is:

1. A method for preparing an embryonated chicken's egg model for the amplification of human or animal circulating tumor cells (CTC), said method comprising
   (i) isolating 5 to 5000 CTC from a sample of a patient or animal having cancer,
   (ii) grafting the 5 to 5000 CTC isolated from the sample on the chorioallantoic membrane (CAM) of an embryonated chicken egg that is at 8 to 10 days of development,
   (iii) incubating the resulting grafted embryonated egg to amplify the CTC to produce a tumor, and
   (iv) collecting the tumor that develops from the amplified CTC.

2. The method for amplifying human or animal circulating tumor cells (CTC) according to claim 1 said method further comprising,
   (v) grafting the tumor collected from step (iv) on the chorioallantoic membrane (CAM) of a second embryonated chicken egg that is at 8 to 10 days of development,
   (vi) incubating said second grafted embryonated egg to obtain a tumor, and
   (vii) collecting the tumor that develops from the grafted tumor from step (vi).

3. The method of claim 1, wherein incubating the resulting grafted embryonated egg in step (iii), comprises incubating the resulting grafted embryonated egg for 48 hours to 20 days.

4. The method of claim 1, further comprising
   (v) isolating CTC from the collected tumor.

5. The method of claim 2, further comprising isolating CTC from the collected tumor.

6. The method of claim 2, wherein incubating said second grafted embryonated egg in step (vi), comprises incubating said second grafted embryonated egg for 48 hours to 20 days.

* * * * *